(12) United States Patent
Lai et al.

(10) Patent No.: US 12,054,699 B2
(45) Date of Patent: Aug. 6, 2024

(54) PERFUSION CELL CULTURE DEVICE AND PERFUSION CELL CULTURE SYSTEM

(71) Applicant: NATIONAL TSING HUA UNIVERSITY, Hsinchu (TW)

(72) Inventors: Wei-Han Lai, Hsinchu (TW); Jen-Huang Huang, Hsinchu (TW); Yu-Lun Lu, Hsinchu (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 450 days.

(21) Appl. No.: 17/354,427

(22) Filed: Jun. 22, 2021

(65) Prior Publication Data

US 2022/0282196 A1    Sep. 8, 2022

(30) Foreign Application Priority Data

Mar. 4, 2021    (TW) .................................. 110107796

(51) Int. Cl.
    *C12M 1/00*    (2006.01)
    *C12M 3/00*    (2006.01)

(52) U.S. Cl.
    CPC ............ *C12M 29/10* (2013.01); *C12M 23/44* (2013.01); *C12M 27/18* (2013.01)

(58) Field of Classification Search
    CPC ...... C12M 29/10; C12M 23/44; C12M 27/18; C12M 23/26; C12M 29/00; C12M 29/12
    See application file for complete search history.

(56) References Cited

U.S. PATENT DOCUMENTS

| 10,160,944 B2 * | 12/2018 | Coppeta ................. C12M 29/10 |
| 2019/0093059 A1 * | 3/2019 | Sugiura ................. C12M 27/00 |

FOREIGN PATENT DOCUMENTS

| CN | 1737157 A | 2/2006 |
| TW | 201139667 A | 11/2011 |
| TW | 201204831 A | 2/2012 |
| WO | WO-2017096285 A1 * | 6/2017 ........ B01L 3/502761 |

OTHER PUBLICATIONS

Wei-Han Lai, "Development of Hydraulically-Driven Microperfusion Cell Culture Platform for High-Throughput Drug Screening", Graduation Thesis Oral Defense for master's degree of Department of Chemical Engineering, National Tsing Hua University, dated on Jun. 24, 2020, oral presentation, Taiwan, R.O.C.

* cited by examiner

*Primary Examiner* — Michael L Hobbs
(74) *Attorney, Agent, or Firm* — Lippes Mathias LLP

(57) ABSTRACT

A perfusion cell culture device includes a driving module and a plurality of cell culture modules. The driving module includes a driving source connecting opening and a chamber. The chamber and the driving source connecting opening are connected. Each of the culture modules includes a fluid channel, a first elastic element, two flow direction controlling units and a cell culture zone. The fluid channel is disposed above the chamber, the first elastic element is disposed between the fluid channel and the chamber, the two flow direction controlling units are respectively disposed on two ends of the fluid channel and connected to the fluid channel selectively, and the cell culture zone is connected to the two flow direction controlling units.

13 Claims, 12 Drawing Sheets

… … …

PERFUSION CELL CULTURE DEVICE AND PERFUSION CELL CULTURE SYSTEM

RELATED APPLICATIONS

This application claims priority to Taiwan Application Serial Number 110107796, filed Mar. 4, 2021, which is herein incorporated by reference.

BACKGROUND

Technical Field

The present disclosure relates to a perfusion cell culture device and a perfusion cell culture system. More particularly, the present disclosure relates to a perfusion cell culture device and a perfusion cell culture system with high-throughput.

Description of Related Art

Cell culturing, which can simply and directly reveal the activities and occurring messages in which of life, has played an important role in modern research field of biomedicine. Cell culturing refers to culture cells in vitro by simulating an appropriate environment in an artificial way. 2D cell culturing, a cell culturing method in early stage, is technically limited by a two dimensional surface, which not only results in an unstable cell growing environment, but is unable to maintain the original shape of cells. Therefore, 3D cell culturing has been developed. Although 3D cell culturing is able to keep cells maintaining their original shape and make cells further proliferate and differentiate, it is unable to simulate practical activities of human body since 3D cell culturing has a lack of circulation mechanism. Therefore, 3D cell culturing cannot effectively approach the real physiological environment, and the technique of perfusion cell culturing has been developed.

The conventional perfusion cell culture system is expensive and complicated to use. In addition, the conventional perfusion cell culture system requires lots of additional devices, such as air compressor, controller and gas cylinder, which make the overall system become bulky and hard to achieve the objective of high-throughput culturing. Therefore, it is important to develop a perfusion cell culture device with high-throughput which conduces to simplifying the system scale.

SUMMARY

According to one aspect of the present disclosure, a perfusion cell culture device includes a driving module and a plurality of cell culture modules. The driving module includes a driving source connecting opening and a chamber. The chamber and the driving source connecting opening are connected. Each of the culture modules includes a fluid channel, a first elastic element, two flow direction controlling units and a cell culture zone. The fluid channel is disposed above the chamber, the first elastic element is disposed between the fluid channel and the chamber, the two flow direction controlling units are respectively disposed on two ends of the fluid channel and connected to the fluid channel selectively, and the cell culture zone is connected to the two flow direction controlling units.

According to another aspect of the present disclosure, a perfusion cell culture system includes a perfusion cell culture device of the aforementioned aspect and a driving source. The driving source is connected to the driving source connecting opening.

BRIEF DESCRIPTION OF THE DRAWINGS

The present disclosure can be more fully understood by reading the following detailed description of the embodiment, with reference made to the accompanying drawings as follows.

DETAILED DESCRIPTION

Figure 1:
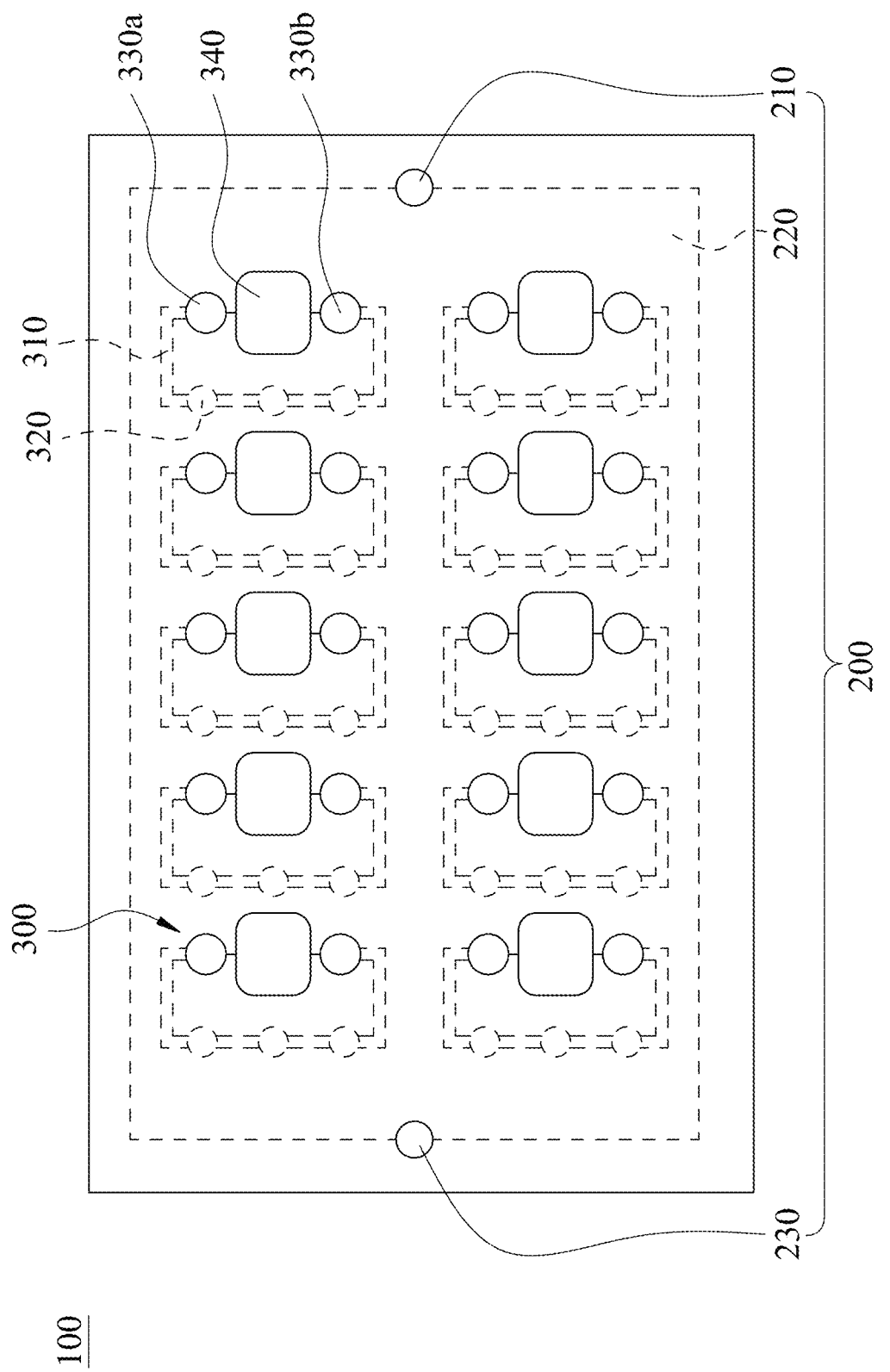
FIG. 1 is a plane view of a perfusion cell culture device according to one aspect of the present disclosure.

Please refer to FIG. 1. FIG. 1 is a plane view of a perfusion cell culture device 100 according to one embodiment of the present disclosure. As shown in FIG. 1, the perfusion cell culture device 100 includes a driving module 200 and a plurality of cell culture modules 300. The driving module 200 includes a driving source connecting opening 210 and a chamber 220, and the chamber 220 and the driving source connecting opening 210 are connected. Each of the cell culture modules 300 includes a fluid channel 310, a first elastic element 320, two flow direction controlling units 330*a*, 330*b* and a cell culture zone 340. The fluid channel 310 is disposed above the chamber 220, the first elastic element 320 is disposed between the fluid channel 310 and the chamber 220, the two flow direction controlling units 330*a*, 330*b* are respectively disposed on two ends of the fluid channel 310, and are selectively connected to the fluid channel 310, and the cell culture zone 340 is connected to the two flow direction controlling units 330a, 330b. According to the aspect of the present disclosure, the first elastic element 320 can be a polymer film, and the fluid channel 310 can contact the polymer film at three positions due to the design of the fluid channel 310, which is shown in FIG. 1.

The driving source connecting opening 210 can externally connect with a driving source so as to apply force to make the first elastic element 320 disposed between the fluid channel 310 and the chamber 220 operate, and further make the fluid in the fluid channel 310 such as culture medium flow due to the pressure change. Further, the two flow direction controlling units 330a, 330b can control the fluid to flow in a single direction to create a cell culturing environment with a circulation mechanism. Moreover, the cells, drugs and culture medium for cell culturing or drug screening can be placed or added in the cell culture zone 340. Besides, the driving module 200 can further include a through hole 230 connecting to the chamber 220, and is used for balancing the pressure in the chamber 220. The through hole 230 can be opened and closed when it is necessary or unnecessary, respectively. The structure and the operation detail of the perfusion cell culture device 100 will be further described in another aspect of the present disclosure, please refer to it.

Figure 2:
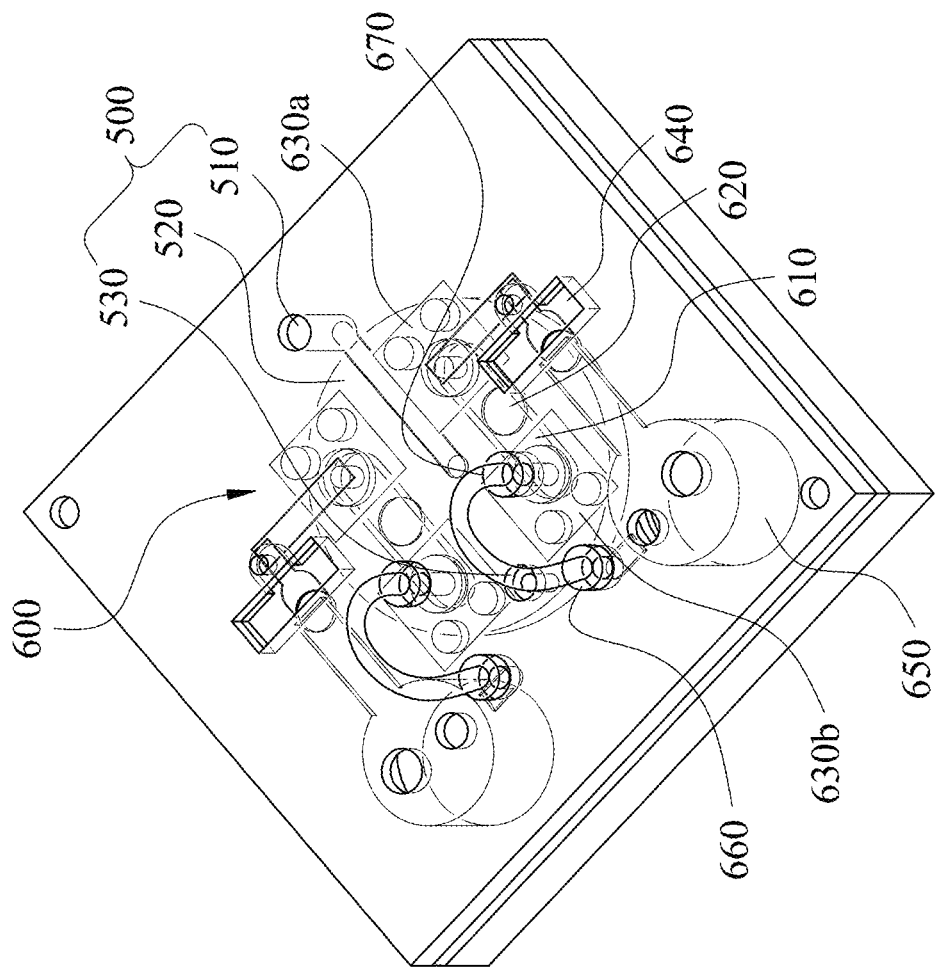
FIG. 2 is a three-dimensional view of a perfusion cell culture device according to another aspect of the present disclosure.
Figure 3:
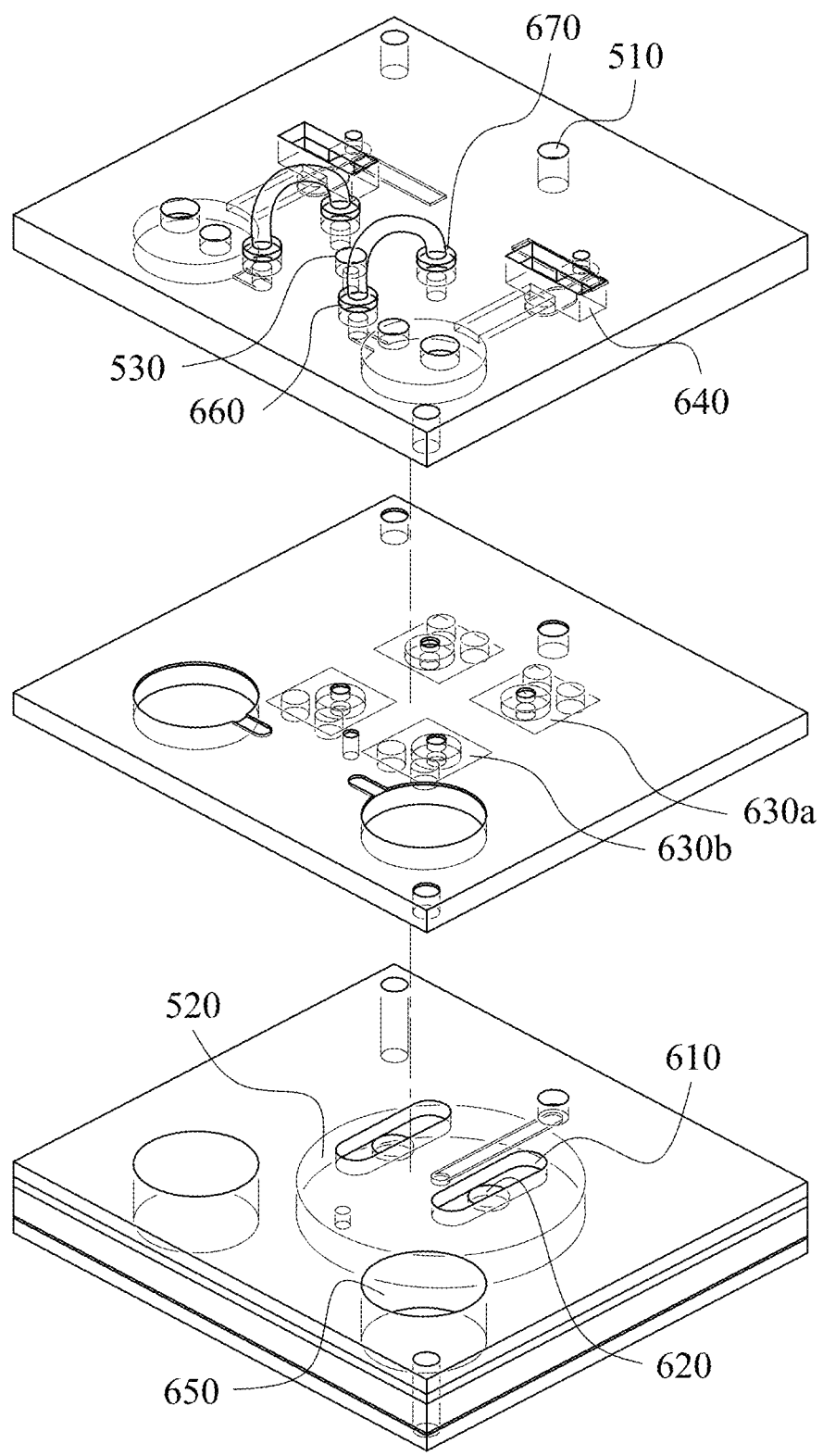
FIG. 3 is a partial exploded view of the perfusion cell culture device of FIG. 2.

Please refer to FIG. 2. FIG. 2 is a three-dimensional schematic view of a perfusion cell culture device 400 according to another aspect of the present disclosure. Please also refer to FIG. 3. FIG. 3 is a partial exploded view of the perfusion cell culture device 400 of FIG. 2. As shown in the figures, the perfusion cell culture device 400 includes a driving module 500 and two cell culture modules 600. The driving module 500 includes a driving source connecting opening 510, a chamber 520 and a through hole 530, and the driving source connecting opening 510, the chamber 520 and the through hole 530 are connected to each other. Each cell culture modules 600 includes a fluid channel 610, a first elastic element 620, two flow direction controlling units 630a, 630b, a cell culture zone 640, a fluid storage tank 650, a fluid outlet 660 and a fluid inlet 670.

The fluid channel 610 is disposed above the chamber 520, and the first elastic element 620 is disposed between the fluid channel 610 and the chamber 520. The two flow direction controlling units 630a, 630b are respectively disposed on two ends of the fluid channel 610, and are selectively connected to the fluid channel 610. The cell culture zone 640 is connected to the flow direction controlling unit 630a. The fluid storage tank 650 is connected to the cell culture zone 640, and is used for storing materials such as culture medium or drugs. The fluid outlet 660 is connected to the fluid storage tank 650. One end of the fluid inlet 670 is connected to the fluid outlet 660 and the other end of the fluid inlet 670 is connected to the flow direction controlling unit 630b. That is, the cell culture zone 640 and the flow direction controlling unit 630a are connected and the cell culture zone 640 is connected to the flow direction controlling unit 630b through the fluid storage tank 650, the fluid outlet 660 and the fluid inlet 670.

In the aspect of the present disclosure, the first elastic element 620 can be made of a polydimethylsiloxane film that a thickness thereof is in a range of 60 μm to 180 μm. Moreover, the fluid can be culture medium. The number of the cell culture modules 600 is two, but the present disclosure is not limited thereto. In other aspects of the present disclosure, the number of the cell culture modules 600 can be four, six, eight, ten or even further more.

Figure 4:
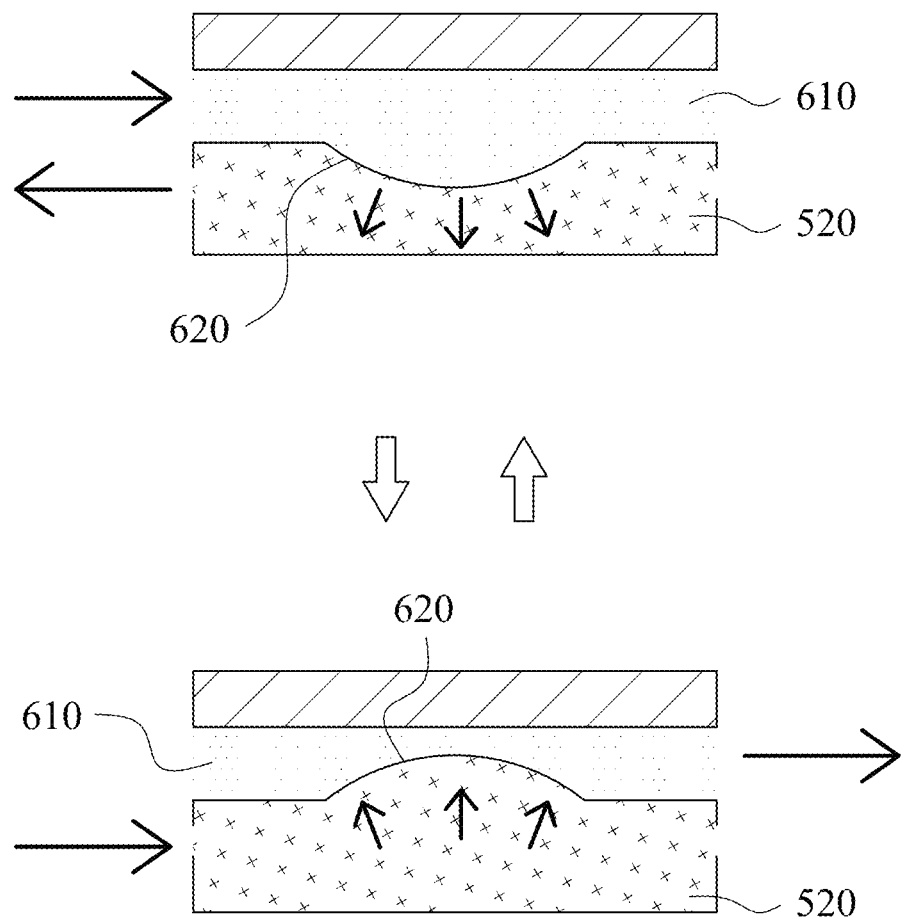
FIG. 4 is an acting view of the perfusion cell culture device of FIG. 2.

Please refer to FIG. 3 and FIG. 4 simultaneously. FIG. 4 is an acting view of the perfusion cell culture device 400 of FIG. 2. As shown in FIGS. 3 and 4, the driving source connecting opening 510 of the perfusion cell culture device 400 is connected to a driving source (not shown), and apply a reciprocating pumping force to the chamber 520 so as to drive the first elastic element 620 disposed between the fluid channel 610 and the chamber 520 waving, and resulting in the fluid (such as culture medium or drugs) stored in the fluid storage tank 650 flowing into the fluid channel 610, and make the fluid flow due to the pressure change.

Figure 5:
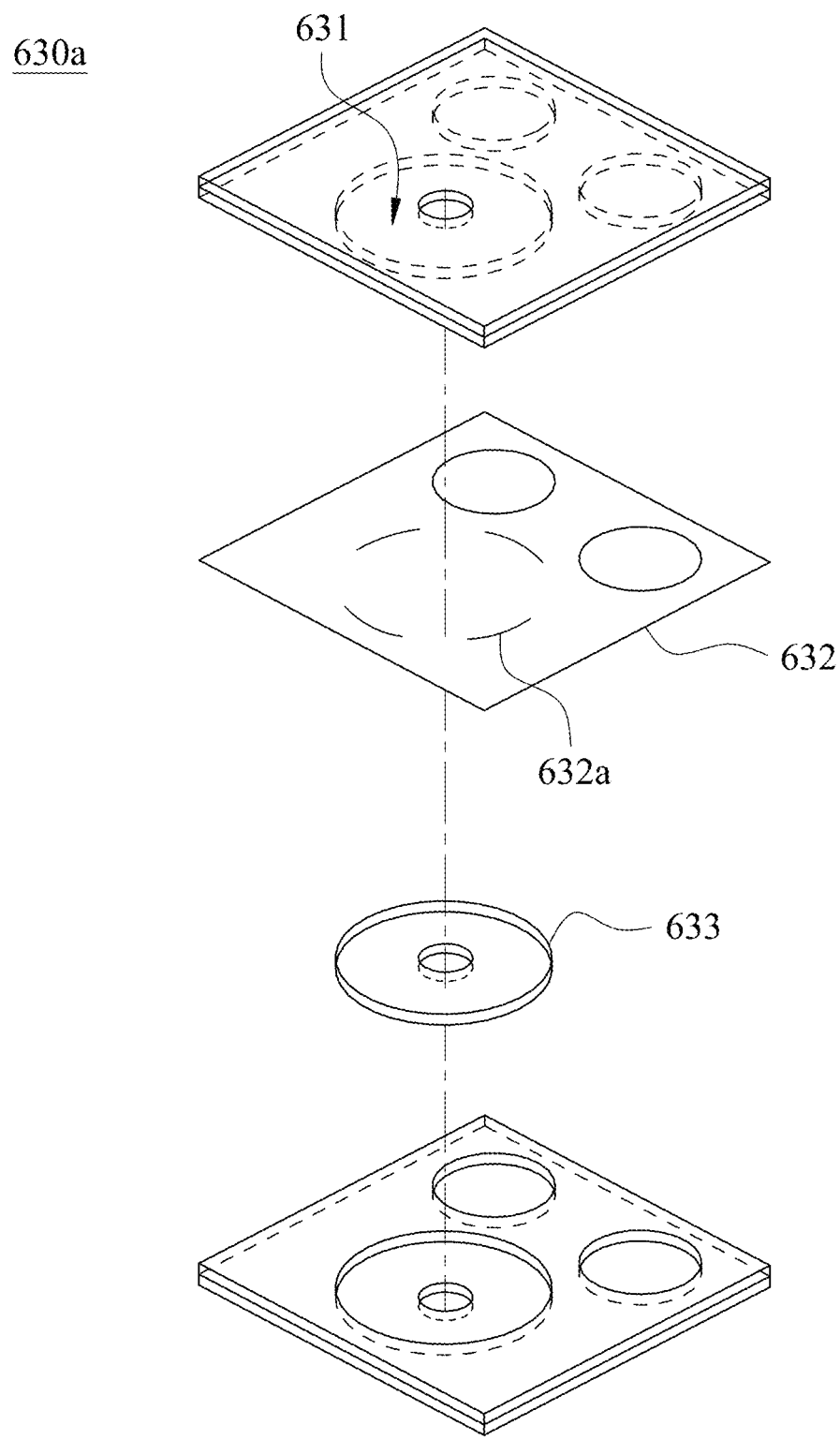
FIG. 5 is a partial exploded view of the flow direction controlling unit of the perfusion cell culture device of FIG. 2.
Figure 6:
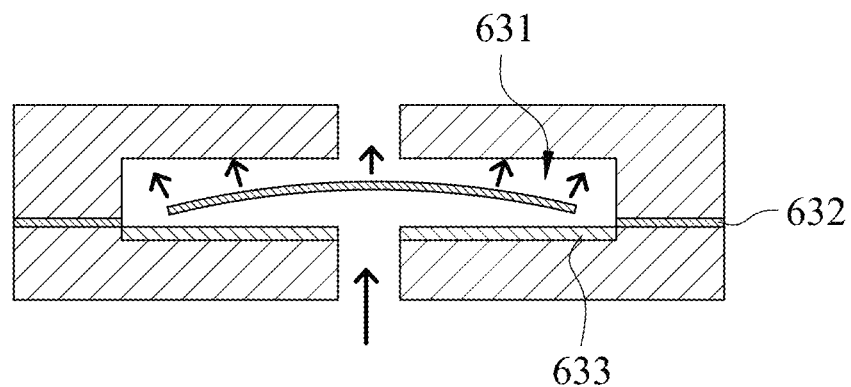
FIG. 6 is an acting view of the flow direction controlling unit of FIG. 5.
Figure 6:
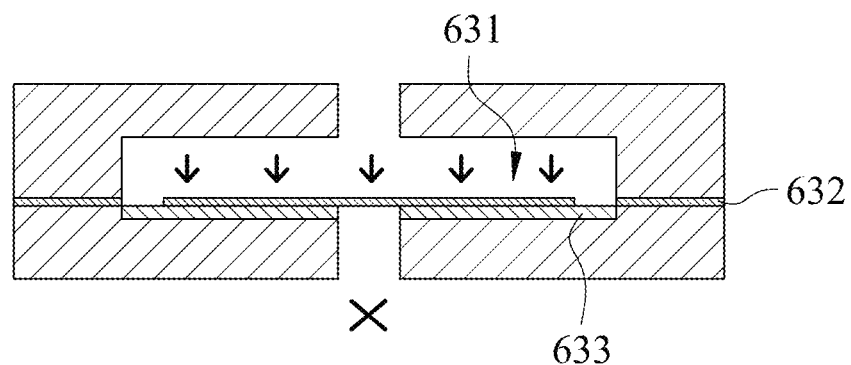

Please refer to FIG. 5. FIG. 5 is a partial exploded view of the flow direction controlling unit 630a of the perfusion cell culture device 400 of FIG. 2. Please also refer to FIG. 6. FIG. 6 is an acting view of the flow direction controlling unit 630a of FIG. 5. As shown in the figures, the flow direction controlling unit 630a includes a flowing space 631, a second elastic element 632 and a polymer dish plate 633. The flowing space 631 and the fluid channel 610 are connected. The second elastic element 632 has at least one slit 632a, and the slit 632a is disposed in the flowing space 631. The polymer dish plate 633 is also disposed in the fluid channel 610 and located on one side of the second elastic element 632.

The slit 632a of the second elastic element 632 is used for connecting the flowing space 631 and the fluid channel 610 selectively. In detail, when a positive pressure is applied to the flow direction controlling unit 630a, the second elastic element 632 in the flowing space 631 stretches therefore, which induces the flowing space 631 being connected to the fluid channel 610 through the slit 632a. On a contrary, when a negative pressure is applied to the flow direction controlling unit 630a, the second elastic element 632 in the flowing space 631 shrinks, and thus blocking the connection between flowing space 631 and the fluid channel 610. Therefore, the flow direction controlling unit 630a can make the fluid flow in a single direction, and to create a cell culturing environment with a circulation mechanism. In the aspect of the present disclosure, the number of the slit 632a is four, and four slits 632a are separated to each other in a same interval distance, but the present disclosure is not limited thereto. As long as the flowing space 631 and the fluid channel 610 can be connected.

In the aspect of the present disclosure, the second elastic element 632 can be made of a polydimethylsiloxane film that a thickness thereof is in a range of 60 μm to 180 μm. Moreover, the polymer dish plate 633 can be used for being attached by the second elastic element 632 during shrinking, to achieve a better sealing effect and reduce the possibility of the fluid backflowing. In the aspect of the present disclosure, the material of the polymer dish plate 633 can be polyethylene terephthalate or polydimethylsiloxane. In other aspects of the present disclosure, the amount of the polymer dish plate 633 can be two, and the materials of the two polymer dish plate 633 are polyethylene terephthalate film and polydimethylsiloxane, respectively, but the present disclosure is not limited thereto.

It is worth to mention that the perfusion cell culture device 400 can be made by microfabrication technology. In detail, laser cutting technology and structure design can be utilized to fabricate the perfusion cell culture device 400 by layer-by-layer stacking method. Materials of each layer of the perfusion cell culture device 400 can be polyethylene terephthalate or polydimethylsiloxane. Therefore, the absorption of the drugs what would like to be detected by the device can be prevent during the drug screening process, and further affect the screening result, that is, since the driving module 500 and the cell culture module 600 of the perfusion cell culture device 400 are both multilayer structure. Thus, the materials of the driving module 500 and the cell culture module 600 can be polyethylene terephthalate, polymethyl methacrylate or a combination thereof, and the materials of the first elastic element 620 and the second elastic element 632 can be further replaced to polydimethylsiloxane. Moreover, each layer of the perfusion cell culture device 400 can be assembled by a biocompatible glue. Therefore, the perfusion cell culture device 400 can be reuse after sterilization by ultra-visible light.

Figure 7:
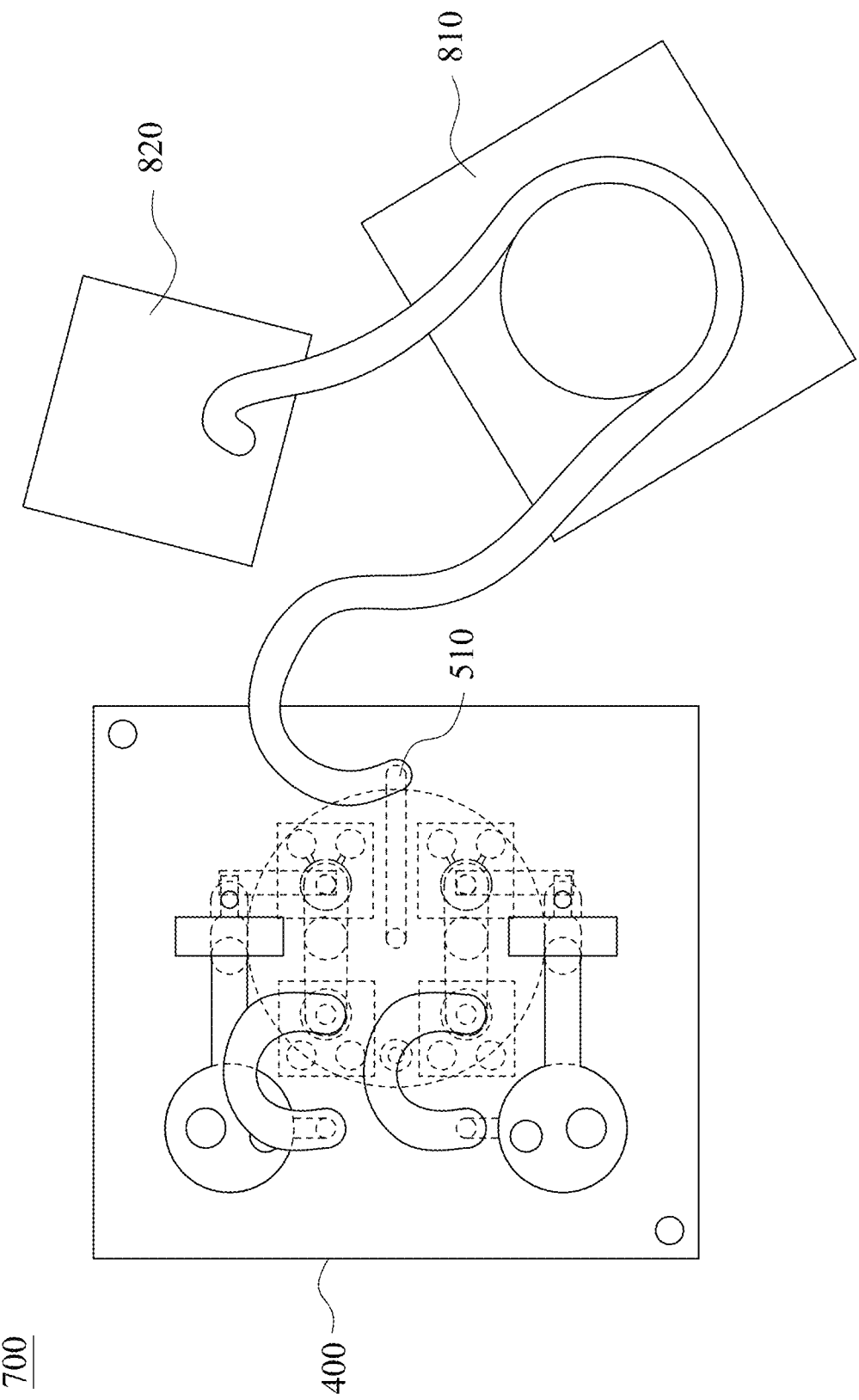
FIG. 7 is a plane view of the perfusion cell culture system according to another aspect of the present disclosure.

Please refer to FIG. 7. FIG. 7 is a plane view of a perfusion cell culture system 700 according to another aspect of the present disclosure. As shown in the figure, the perfusion cell culture system 700 includes the perfusion cell culture device 400 of FIG. 2, a driving source 810 and an auxiliary driving unit 820. The driving source 810 is connected to the driving source connecting opening 510 of the perfusion cell culture device 400, and the auxiliary driving unit 820 is connected to the driving source 810. In the aspect of the present disclosure, the driving source 810 can be a peristaltic pump and the auxiliary driving unit 820 can be a water tank. Please refer to the mentioned aspect of the present disclosure for the detail information of the perfusion cell culture device 400, which is not further described here.

Figure 8:
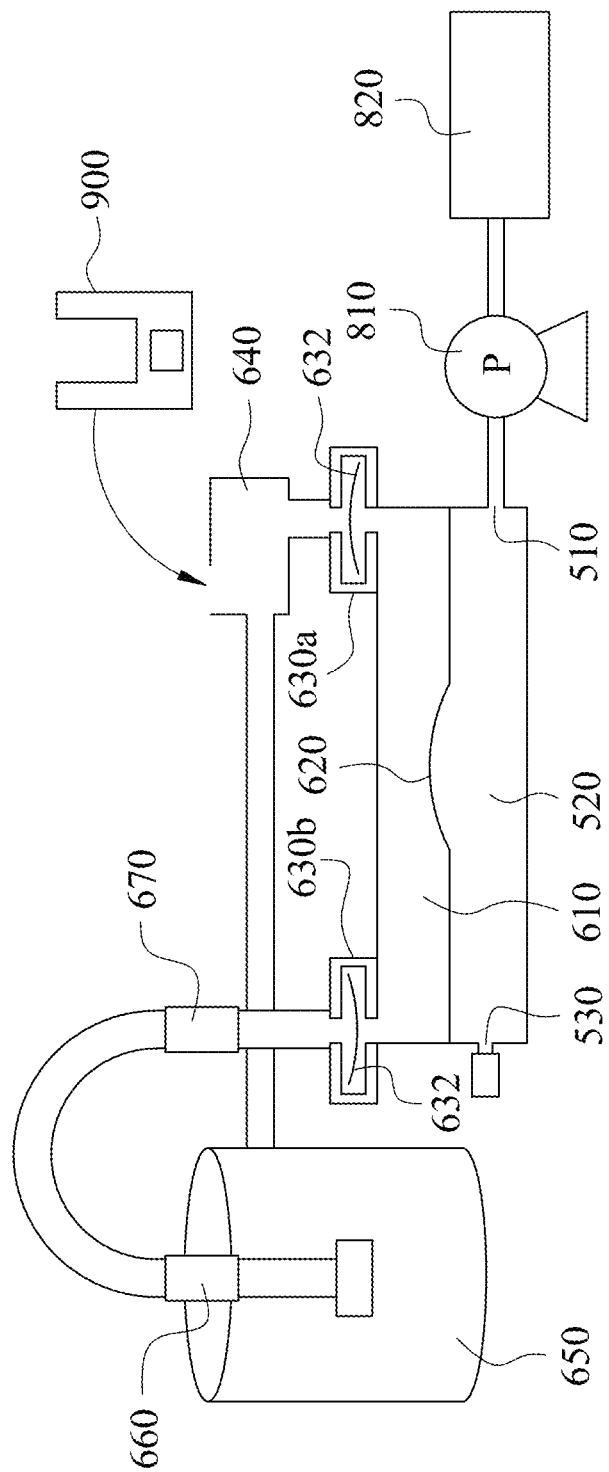
FIG. 8 is a partial acting view of the perfusion cell culture system of FIG. 7.

Please also refer to FIG. 8. FIG. 8 is a partial acting view of the perfusion cell culture system 700 of FIG. 7. First of all, the through hole 530 can be opened before the water flows into the chamber 520 to balance the pressure so as to fulfill the chamber 520 by water. After that, the through hole 530 will be closed. Then, the driving source 810 collocates with the auxiliary driving unit 820 and pumps the water in the chamber 520 back and forth, and thus the first elastic element 620 disposed between the fluid channel 610 and the chamber 520 waves, which further makes the fluid (such as culture medium) in the fluid channel 610 flow. Further, the flow of the fluid applies a positive pressure to the flow direction controlling unit 630*a* and stretches the second elastic element 632. Therefore, the fluid in the fluid channel 610 can pass through the flow direction controlling unit 630*a* and get into the cell culture zone 640, and pass through the fluid storage tank 650, the fluid outlet 660 and the fluid inlet 670, and flows into another flow direction controlling unit 630*b* and return to the fluid channel 610 afterwards, which construct a cell culturing environment with circulation mechanism. In the aspect of the present disclosure, the shape and the size of the cell culture zone 640 can correspond to a known plugging-unplugging type cell culturing unit 900 placed in the cell culture zone 640 so as to carry out cell culturing or drug screening, but the present disclosure is not limited thereto.

It is worth to mention that as long as the driving source 810 can apply a force to the chamber 520 of the driving module 500 to wave the first elastic element 620 of the cell culture module 600, so that the arrangement of the auxiliary driving unit 820 is not essential. For example, in other aspects of the present disclosure, the driving source 810 can be a pump like a peristaltic pump, a syringe pump or a diaphragm pump, by pumping air to the chamber 520 of the driving module 500 to wave the first elastic element 620 so as to promoting the fluid in the fluid channel 610 flows.

Figure 9B:
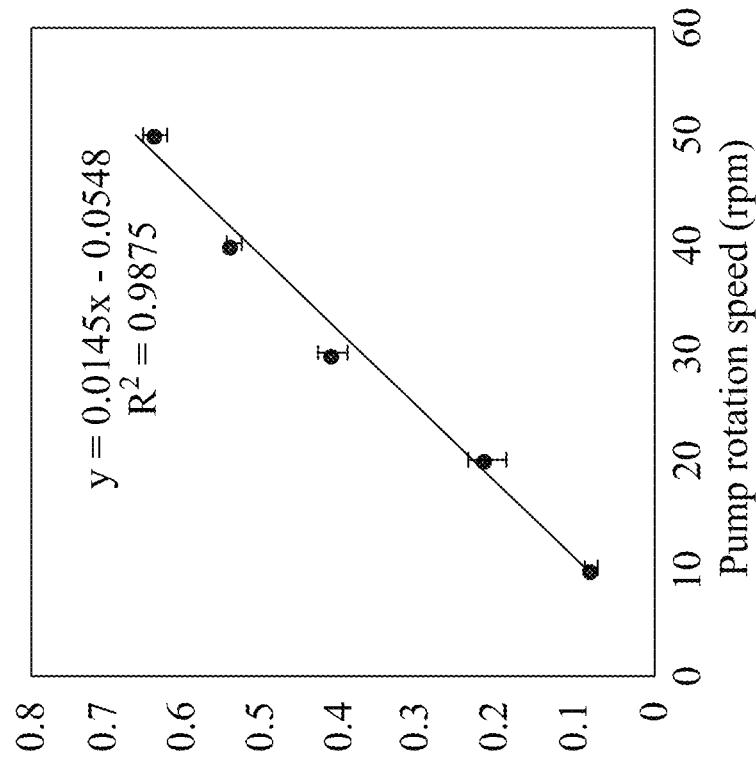
FIG. 9B is an analysis diagram of the average fluid flow rate of the two cell culture modules of the perfusion cell culture system of FIG. 7 under different rotation speed of the pump.
Figure 9A:
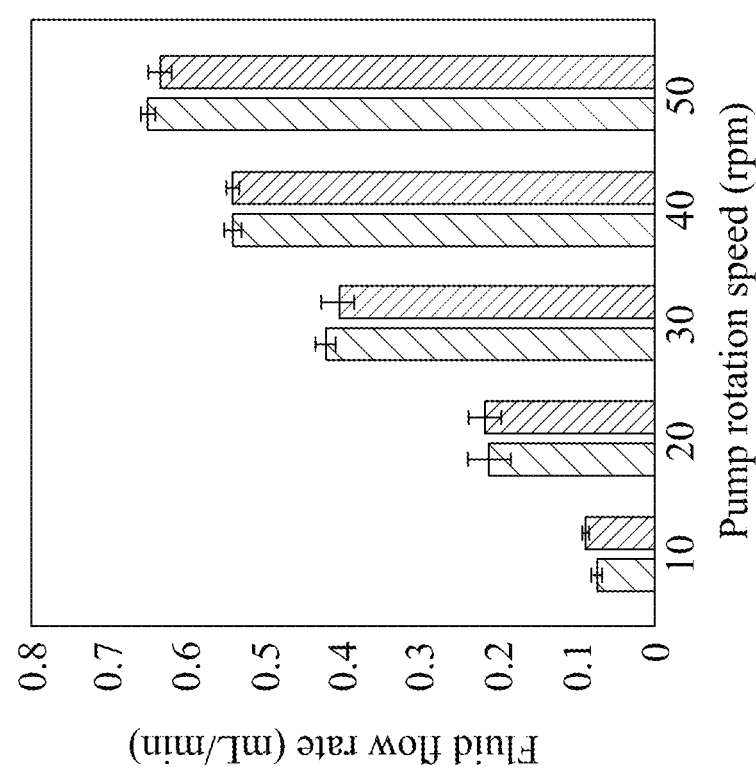
FIG. 9A is an analysis diagram of the fluid flow rate of the two cell culture modules of the perfusion cell culture system of FIG. 7 under different rotation speed of the pump.

Please refer to FIG. 9A and FIG. 9B, which are analysis diagrams of the fluid flow rate and the average fluid flow rate of the two cell culture modules 600 of the perfusion cell culture system 700 of FIG. 7 under different rotation speed of the pump, respectively. As shown in the figures, the two cell culture modules 600 of the perfusion cell culture system 700 have similar fluid flow rate under different rotation speed of the pump, which indicates that the perfusion cell culture system 700 is able to supply fluid to each of the cell culture modules 600, and the culturing concentration in each of the cell culture modules 600 is similar thereby. The rotation speed of the pump and the average fluid flow rate show a linear relationship, which also indicates that the fluid flow rate of the perfusion cell culture system 700 can be controlled by changing the rotation speed of the pump.

Figure 10:
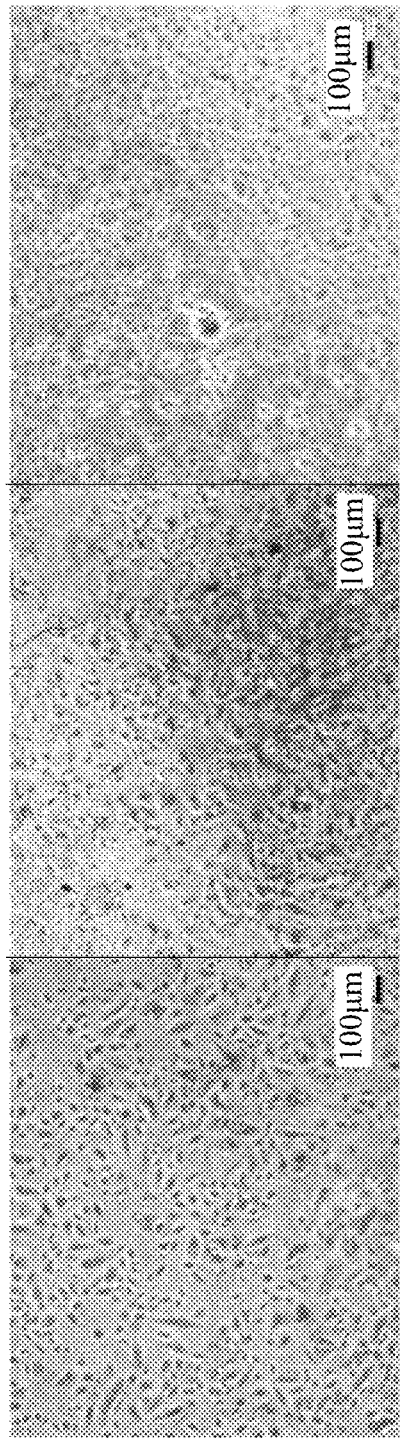
FIG. 10 shows microscopy images of the A549 cells proliferated in the perfusion cell culture system of FIG. 7.
Figure 11B:
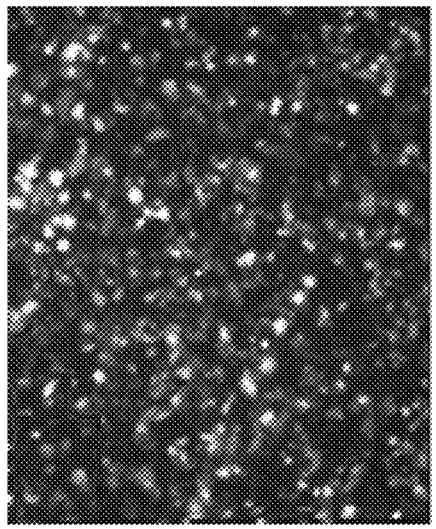
FIG. 11A and FIG. 11B show microscopy images of the A549 cells before received medicine in the perfusion cell culture system of FIG. 7.
Figure 11D:
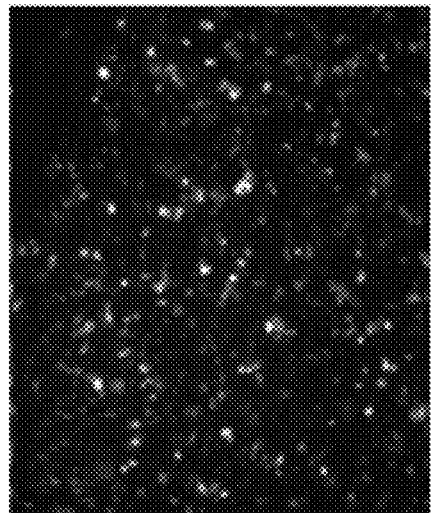
FIG. 11D shows a microscopy image of the A549 cells in the perfusion cell culture system of FIG. 7 for one day after received medicine.
Figure 11A:
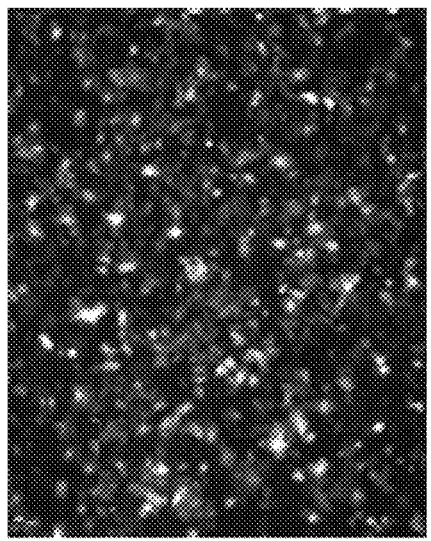
Figure 11C:
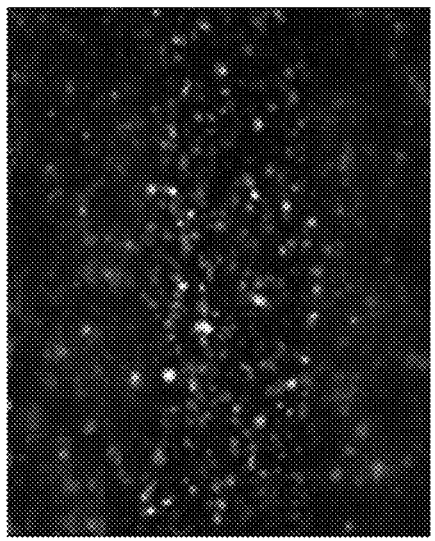
FIG. 11C shows a microscopy image of the A549 cells in the perfusion cell culture system of FIG. 7 for one day.

Please refer to FIG. 10. FIG. 10 shows microscopy images of the A549 cells proliferated in the perfusion cell culture system 700 of FIG. 7, wherein the scale bar represents 100 μm. As shown in the figure, the A549 cells have proliferated in three days and reach about 90% confluence, that is, the A549 cells can proliferate in the perfusion cell culture system 700 of present disclosure stably and continuously. Please refer to FIG. 11A, FIG. 11B, FIG. 11C, and FIG. 11D. FIG. 11A and FIG. 11B show microscopy images of the A549 cells before received medicine in the perfusion cell culture system 700 of FIG. 7. FIG. 11C shows a microscopy image of the A549 cells in the perfusion cell culture system 700 of FIG. 7 for one day. FIG. 11D shows a microscopy image of the A549 cells in the perfusion cell culture system 700 of FIG. 7 for one day after received medicine. The received medicine, Cisplatin, is a chemotherapy agent for cancer. It can be observed from the figure that the most of the A549 cells are dead for one day after receiving Cisplatin.

Figure 12:
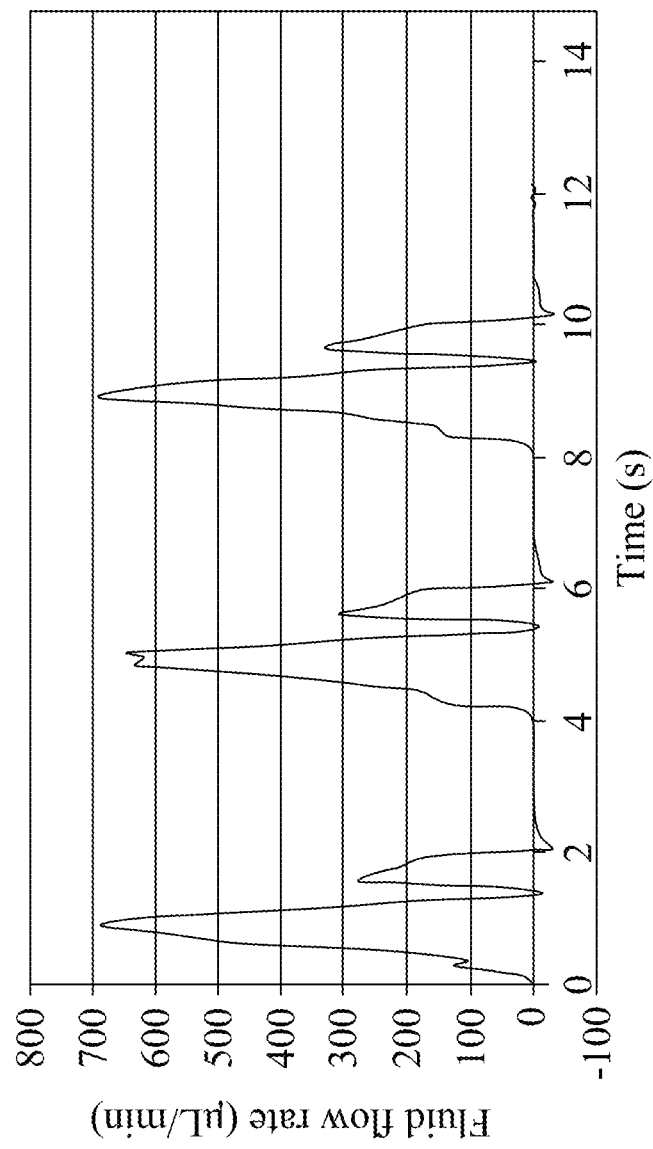
FIG. 12 is a flowing pattern analysis diagram of the perfusion cell culture system according to further another aspect of the present disclosure when the pump rotation speed is 10 RPM.

Please refer to FIG. 12. FIG. 12 is a flowing pattern analysis diagram of the perfusion cell culture system according to further another aspect of the present disclosure when the pump rotation speed is 10 RPM. As shown in the figure, the flowing of the fluid in the perfusion cell culture system of the present disclosure is similar to the human blood flowing into and out of the blood vessels, which indicates that the perfusion cell culture system of the present disclosure can further close to actual physiological environment.

In summary, the perfusion cell culture device of the present disclosure can simultaneously drive the fluid in each of the cell culture modules flows by using a single driving source. The perfusion cell culture device cooperates with the flow direction controlling units disposed on two ends of each of the fluid channel, which can form a cell culturing environment with circulation mechanism with each of the cell culture zone, and multiple sets of the perfusion cell culturing process can be carried out simultaneously. Moreover, each unit of the perfusion cell culture device, such as the fluid channel and the fluid storage tank, can have different shape or size to each other and can also be adjusted on demand, which achieves the goal of culturing cells under different conditions in the same time. Therefore, the perfusion cell culture device of the present disclosure can achieve not only the objective of high-throughput and simplifying the system scale, but is also conductive to long term cell culturing or drug screening, which is helpful to the research of the diseases such as cancer.

Besides, the perfusion cell culture system of the present disclosure can carry out multiple sets of the perfusion cell culturing process by one single driving source, which is simple to operate. In contrast to the conventional perfusion cell culture system, the perfusion cell culture system of the present disclosure can further reduce the cost and the needed space of the apparatus.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A perfusion cell culture device, comprising:
   a driving module, comprising:
      a driving source connecting opening; and
      a chamber, wherein the driving source connecting opening and the chamber are connected; and
   a plurality of cell culture modules, each of the cell culture modules comprising:
      a fluid channel disposed above the chamber;
      a first elastic element disposed between the fluid channel and the chamber;
      two flow direction controlling units respectively disposed on two ends of the fluid channel and connected to the fluid channel selectively;
      a cell culture zone connected to the two flow direction controlling units;
      a fluid storage tank connected to the cell culture zone;
      a fluid outlet connected to the fluid storage tank; and
      a fluid inlet, wherein one end of the fluid inlet is connected to the fluid outlet and the other end of the fluid inlet is connected to one of the two flow direction controlling units;
   wherein the cell culture zone is connected to the other one of the two flow direction controlling units and is connected to one of the two flow direction controlling units through the fluid storage tank, the fluid outlet and the fluid inlet;
   wherein each of the two flow direction controlling units comprises a flowing space connected to the fluid channel and a second elastic element having at least one slit, and the at least one slit is disposed in the flowing space and is for connecting the flowing space and the fluid channel selectively;
   when a positive pressure is applied to each of the two flow direction controlling units, the second elastic element in the flowing space stretches, so that the flowing space is connected to the fluid channel through the at least one slit; and
   when a negative pressure is applied to each of the two flow direction controlling units, the second elastic element in the flowing space shrinks, so that the flowing space and the fluid channel are not connected.

2. The perfusion cell culture device of claim 1, wherein the first elastic element is a polymer film.

3. The perfusion cell culture device of claim 2, wherein a material of the polymer film is polydimethylsiloxane, and a thickness of the polymer film is in a range of 60 μm to 180 μm.

4. The perfusion cell culture device of claim 1, wherein both the first elastic element and the second elastic element are polymer films.

5. The perfusion cell culture device of claim 4, wherein a material of each of the first elastic element and the second elastic element is a polydimethylsiloxane film, and a thickness of each of the first elastic element and the second elastic element is in a range of 60 μm to 180 μm.

6. The perfusion cell culture device of claim 1, wherein each of the two flow direction controlling units further comprises:
   at least one polymer dish plate disposed in the flowing space and located at one side of the second elastic element.

7. The perfusion cell culture device of claim 6, wherein a material of the polymer dish is polydimethylsiloxane or polyethylene terephthalate.

8. The perfusion cell culture device of claim 1, wherein the driving module further comprises a through hole connecting the driving module and the chamber.

9. The perfusion cell culture device of claim 1, wherein a material of each of the driving module and the cell culture modules is polyethylene terephthalate, polymethyl methacrylate or a combination thereof.

10. A perfusion cell culture system, comprising:
    the perfusion cell culture device of claim 1; and
    a driving source connected to the driving source connecting opening.

11. The perfusion cell culture system of claim 10, wherein the driving source is a pump.

12. The perfusion cell culture system of claim 10, wherein the driving source is a peristaltic pump, a syringe pump or a diaphragm pump.

13. The perfusion cell culture system of claim 10, further comprising:
    an auxiliary driving unit connected to the driving source;
    wherein the driving source is a pump and the auxiliary driving unit is a water tank.

* * * * *